(12) United States Patent
Tortelli et al.

(10) Patent No.: US 8,822,741 B2
(45) Date of Patent: Sep. 2, 2014

(54) PROCESS FOR THE FLUORINATION OF HALOOLEFINS

(75) Inventors: Vito Tortelli, Milan (IT); Marco Galimberti, Milan (IT)

(73) Assignee: Solvay Specialty Polymers Italy S.p.A., Bollate (Milano) (IT)

(*) Notice: Subject to any disclaimer, the term of this patent is extended or adjusted under 35 U.S.C. 154(b) by 0 days.

(21) Appl. No.: 13/809,486

(22) PCT Filed: Jul. 5, 2011

(86) PCT No.: PCT/EP2011/061264
§ 371 (c)(1),
(2), (4) Date: Jan. 10, 2013

(87) PCT Pub. No.: WO2012/007310
PCT Pub. Date: Jan. 19, 2012

(65) Prior Publication Data
US 2013/0116483 A1    May 9, 2013

(30) Foreign Application Priority Data
Jul. 13, 2010 (EP) .................................... 10169355

(51) Int. Cl.
*C07C 41/22*  (2006.01)
*C07C 17/04*  (2006.01)
*C07C 21/04*  (2006.01)
*C07C 21/08*  (2006.01)
*C07C 21/10*  (2006.01)
*C07C 21/18*  (2006.01)

(52) U.S. Cl.
CPC ................ *C07C 17/04* (2013.01); *C07C 41/22* (2013.01)
USPC ........... 570/164; 570/170; 570/231; 570/234; 570/246; 570/252

(58) Field of Classification Search
CPC ....................................................... C07C 17/04
USPC ......................................... 570/161, 164, 252
See application file for complete search history.

(56) References Cited

U.S. PATENT DOCUMENTS

| 3,882,178 A | 5/1975 | Benninger et al. |
| 3,962,348 A | 6/1976 | Benninger et al. |
| 5,965,779 A | 10/1999 | Otsuka et al. |
| 6,191,326 B1 | 2/2001 | Otsuka et al. |
| 7,674,939 B2 * | 3/2010 | Mukhopadhyay et al. ... 570/156 |

FOREIGN PATENT DOCUMENTS

| EP | 0396168 A1 | 11/1990 |
| EP | 396168 A1 * | 11/1990 |

OTHER PUBLICATIONS

Moldayskii, D. D. et al. Journal of Fluorine Chemistry 1999, 94, 157-167.*
Hutchinson, John, et al—"Elemental Fluorine in Organic Chemistry", 1997, Topics in Current Chemistry, vol. 193. Springer Verlag Berlin Heidelberg, pp. 1-43; 43 pgs.
Sandford, G.—"Elemental Fluorine in Organic Chemistry (1997-2006)", 2007, Journal of Fluorine Chemistry, vol. 128. Issue No. 2, Elsevier NL. pp. 90-104; 15 pgs.
Conte L., et al—"Fluorination of Hydrogen-Containing Olefins with Elemental Fluorine", 1988, Journal of Fluorine Chemistry, Elsevier Sequoia, NL, vol. 38, pp. 319-326; 8 pgs.
Drakesmith, F.G., et al—"Electrochemical Fluorination Using Porous Nickel and Foam Nickel Anodes", 1986, Journal of Fluorine Chemistry, vol. 32, Issue No. 1, Elsevier Sequoia, NL, pp. 103-134; 32 pgs.
Rozen S., et al—"Eemenal Fluorine as a Fluorinating Agent and as an Oxidizer in Organic Chemistry", 1987, Journal of Fluorine Chemistry, vol. 35, Issue No. 1. pp. 9; 1 pg.
Chambers, Richard D., et al—"Electrophilic Fluorination Using Elemental Fluorine", 1995, Journal of the Chemical Society. Chemical Communications, vol. 1, pp. 17: 1 pg.
Chambers, Richard D., et al, "Elemental fluorine. Part 1. Synthesis of fluoroaromatic compounds", 1996, Journal of the Chemical Society, Perkin Transactions 1: Organic and Bio-Organic Chemistry, vol. 7. pp. 605-609: 5 pgs.
Moldavskii, Dmitrii D., et al—"Technology for the preparation of perfluoro-organic compounds", 1999, Journal of Fluorine Chemistry, vol. 94, Issue No. 2, Elsevier Science SA, pp. 157-167: 11 pgs.

* cited by examiner

*Primary Examiner* — Jafar Parsa
*Assistant Examiner* — Medhanit Bahta

(57) ABSTRACT

A process for the fluorination of haloolefins with elemental fluorine in the presence of anhydrous HF proceeds with high yield and selectivity in the product deriving from the addition of fluorine to the carbon-carbon double bond.

10 Claims, No Drawings

PROCESS FOR THE FLUORINATION OF HALOOLEFINS

CROSS-REFERENCE TO RELATED APPLICATIONS

This application is a U.S. national stage entry under 35 U.S.C. §371 of International Application No. PCT/EP2011/061264 filed Jul. 5, 2011, which claims priority to European application No. 10169355.4 filed on Jul. 13, 2010, the whole content of this application being incorporated herein by reference for all purposes.

TECHNICAL FIELD

The invention relates to a process for the addition of elemental fluorine to haloolefins.

BACKGROUND ART

The use of elemental fluorine as fluorinating agent for the preparation of fluorinated compounds is well known, see for instance HUTCHINSON, John, et al. Elemental Fluorine in Organic Chemistry. *Topics in Current Chemistry*. 1997, vol. 193, p. 1-43.

Addition of elemental fluorine to carbon-carbon double bonds has been previously described: see for example HUTCHINSON, John, et al. Elemental Fluorine in Organic Chemistry. *Topics in Current Chemistry*. 1997, vol. 193, p. 1-43; SANDFORD, Graham. Elemental Fluorine in Organic Chemistry (1997-2006). *J. Fluorine Chem.* 2007, vol. 128, p. 90-104.

Many olefins, including haloolefins, are readily available in commercial quantities, thus the fluorination of olefins to produce fluorinated saturated products would be commercially useful. However, the fluorination reaction of unsaturated compounds is highly exothermic and violent in nature. The high exothermicity of the reaction can lead to strong increases of the reaction temperature, within very short times, and is therefore difficult to control. Locally the temperature can be so high as to cause the scission of carbon-carbon bonds, leading to the formation of undesired by-products. Another occurring drawback of the direct addition of fluorine to olefins is the dimerization of the reaction product.

To control the reaction, the fluorination of olefins has been typically carried out at a very low temperature, in the presence of a solvent and with a very low concentration of elemental fluorine, heavily diluted with an inert gas. This process suffers from low productivity without significant alteration of the fluorination mechanism; in other words, selectivity in the fluorine addition product tends to remain low. See for instance, CONTE, L., et al. Fluorination of hydrogen-containing olefins with elemental fluorine. *Journal of Fluorine Chemistry*. 1988, vol. 38, p. 319-326. wherein the reaction of addition of fluorine to chloroolefins was carried out employing very low concentrations of fluorine in the presence of apolar solvents resulting in low selectivity in the addition product.

Alternatively, control of the fluorine addition process has been disclosed in EP 396168 A (PCR, INC.) Jul. 11, 1990 by carrying out the reaction in an eductor, i.e. a jet pump that allows addition of fluorine at very high flow rates, thereby promoting rapid circulation of the reaction mixture in the cooling system. The rapid circulation of the reaction fluids prevents the formation of hot-spots as well as the occurrence of side-reactions.

There is thus still a need in the art for a process for addition of fluorine to olefins, in particular haloolefins, providing high yields and productivity. Additionally, there is still a need for a process providing high yields and productivity without requiring the use of complex equipment.

DISCLOSURE OF INVENTION

It has now surprisingly been found that when the fluorination reaction of a haloolefin is carried out in the presence of anhydrous HF it is possible to operate with higher fluorine concentrations, thus increasing the reaction rate, and with reduced incidence of parasitic reactions, thus improving the yield in the fluorine addition product.

It is thus an object of the present invention to provide a process for the fluorination of haloolefins, which advantageously proceeds with high yield and selectivity.

The term "haloolefin" is used herein to refer to any straight-chain, or branched compound comprising at least one carbon-carbon double bond and wherein at least one carbon atom of said double bond forms no more than one carbon-hydrogen bond. Preferably at least one carbon atom of the haloolefin double bond forms a carbon-halogen bond.

Any haloolefin as above defined may be fluorinated with the present process.

According to one embodiment the process of the invention comprises reacting a haloolefin of formula (I) with elemental fluorine in the presence of anhydrous HF:

$$CXR^1 = CYR^2 \qquad (I)$$

wherein:
- $R^1$ is selected from the group consisting of F, Cl, Br, I, $R_{f1}$, $OR_{f1}$;
- $R^2$ is selected from the group consisting of H, F, Cl, Br, I, $R_{f2}$, $OR_{f2}$;
- X is selected from the group consisting of H, F, Cl, Br, I; and
- Y is selected from the group consisting of H, F, Cl, Br, I; and
- $R_{f1}$ and $R_{f2}$ groups, equal to or different from each other, are independently selected from a straight-chain or branched $C_1$-$C_{20}$ fluoroalkyl or a $C_1$-$C_{20}$ fluorooxyalkyl, comprising one or more than one catenary oxygen atoms; $R_{f1}$ and $R_{f2}$ may be comprised in a fluorinated cycloalkyl structure.

When a fluoroalkyl, $R_{f1}$ and $R_{f2}$, equal to or different from each other, are preferably selected from a $C_1$-$C_{10}$ fluoroalkyl, more preferably a $C_1$-$C_5$ fluoroalkyl, even more preferably a $C_1$-$C_3$ fluoroalkyl.

When a fluorooxyalkyl, $R_{f1}$ and $R_{f2}$, equal to or different from each other, are preferably selected from a $C_1$-$C_{10}$ fluorooxyalkyl.

In a preferred embodiment $R_{f1}$ and $R_{f2}$ are fully fluorinated, i.e. perfluorinated.

The main product that forms in the reaction is $$CFXR^{1*}CFYR^{2*} \qquad (II).$$

In formula (II) $R^{1*} = R^1$ when $R^1$ is selected from F, Cl, Br, I and when $R_{f1}$ or $OR_{f1}$ is perfluorinated and $R^{2*} = R^2$ when $R^2$ is selected from H, F, Cl, Br, I and when $R_{f2}$ or $OR_{f2}$ is perfluorinated. When $R_{f1}$ and/or $R_{f2}$ ($OR_{f1}$ and/or $OR_{f2}$) are not fully fluorinated $R^{1*}$ and/or $R^{2*}$ may differ from $R^1$ and/or $R^2$ in that partial or complete replacement of the hydrogen atoms in $R_{f1}$ and/or $R_{f2}$ may take place.

In formula (I) and (II) above:
- $R^1$ is preferably selected from the group consisting of F, Cl, $R_{f1}$, $OR_{f1}$;

$R^2$ is preferably selected from the group consisting of H, F, Cl, $R_{f2}$, $OR_{f2}$;

X is preferably selected from the group consisting of H, F, Cl;

Y is preferably selected from the group consisting of H, F, Cl; and $R_{f1}$ and $R_{f2}$ are as defined.

According to one embodiment of the process Y is H, so that the process comprises reacting a haloolefin of formula (Ia) with elemental fluorine in the presence of anhydrous HF:

$$CXR^1 \!\!=\!\! CHR^2 \tag{Ia}$$

wherein $R^1$, $R^2$, X, $R_{f1}$ and $R_{f2}$ are as above defined.

Preferably, when X is H then $R^2$ is F or Cl, preferably Cl.

The process proceeds with high conversion of the haloolefin (Ia) and high yield in the fluorine addition product (IIa) $CFXR^{1*}CHFR^{2*}$. In formula (IIa) $R^{1*}$ and $R^{2*}$ are as above defined, preferably $R_{f1}$ and $R_{f2}$ are perfluorinated.

The occurrence of parasitic reactions, such as dimerization and/or isomerization of the addition product which is generally observed in fluorine addition reactions to haloolefins is greatly reduced as shown by the increased selectivity of the process towards the formation of the addition product (II)/(IIa).

Examples of haloolefins that can be fluorinated with the present process are for instance: $CH_2\!\!=\!\!CCl_2$, $CHCl\!\!=\!\!CCl_2$, $CHCl\!\!=\!\!CHCl$, $CFCl\!\!=\!\!CHF$, $CF_3OCH\!\!=\!\!CFCl$, $CF_3OCCl\!\!=\!\!CHF$, $CF_3CCl\!\!=\!\!CF_2$, $CF_3CCl\!\!=\!\!CF_2$.

Preferably, the haloolefin is selected from the group consisting of $CH_2\!\!=\!\!CCl_2$, $CHCl\!\!=\!\!CCl_2$, $CHCl\!\!=\!\!CHCl$, $CF_3OCH\!\!=\!\!CFCl$. More preferably the haloolefin is $CHCl\!\!=\!\!CCl_2$ or $CHCl\!\!=\!\!CHCl$.

Generally fluorine is added to the haloolefin in an amount equal to or lower than the stoichiometric amount necessary to convert all carbon-carbon double bonds in the olefin.

Fluorine may be fed into the reaction vessel as a pure gas or diluted with an inert gas, such as nitrogen, argon and helium. Typically, fluorine is diluted with an inert gas. When an inert gas is used, the concentration of fluorine in the gas feed ranges from 10 to 90% by volume, preferably from 15 to 70% by volume, more preferably from 20 to 60% by volume.

Anhydrous HF is preferably used as the sole reaction medium in the process. Alternatively, the process may be carried out in the presence of a suitable diluent, in addition to anhydrous HF. Suitable diluents are those compounds which are inert to both elemental fluorine and anhydrous HF and which are liquid at the reaction temperature, such as perchlorofluoroalkanes, perfluoropolyethers and perfluoroethers. When a diluent is used, the ratio by volume of anhydrous HF to the diluent is at least 1:1, preferably at least 2:1, more preferably at least 5:1, even more preferably at least 10:1.

Typically, fluorine and the haloolefin, in separate feeds, are continuously fed to the reaction vessel containing anhydrous HF at the given temperature of the process. Alternatively, the haloolefin may be dissolved in the reaction medium before the addition of fluorine.

Typically the ratio by volume of anhydrous HF to the diluent is at least 2:1

The end of the reaction can be advantageously detected by online analysis, by checking fluorine consumption.

The reaction may be conducted over a wide temperature range. Generally, a temperature range of from −90 to 0° C. may be employed. Preferably, the reaction is conducted at a temperature of from −80 to −20° C.

In general at the end of the process two phases form in the reaction vessel, the upper one consisting mainly of anhydrous HF which can easily be separated from the reaction products and recycled in the process. The product may be recovered by standard separation and purification procedures from the remaining phase.

Should the disclosure of any of the patents, patent applications, and publications that are incorporated herein by reference conflict with the present description to the extent that it might render a term unclear, the present description shall take precedence.

The invention will be now described in more detail with reference to the following examples, whose purpose is merely illustrative and not intended to limit the scope of the invention.

EXAMPLES

Example 1

In a 250 ml stainless steel reactor containing 59 g of anhydrous hydrogen fluoride (aHF) kept under vigorous stirring at −70° C., trichloroethylene (6 ml/h) and fluorine (1.53 Nl/h diluted with 4.5 Nl/h of helium) were fed for 4 hours; after this period, the crude mixture was transferred in a stainless steel cylinder and the organic layer analyzed.

The conversion of trichloroethylene was 84% while the selectivity towards the formation of $CHClF\!\!-\!\!CCl_2F$ was 83%.

Other products obtained in the process and their relative quantities were: $F(C_2Cl_3H)_2F$ (6%), $CF_2ClCFCl_2$ (2%).

Comparative Example 1

The same reaction described in Example 1 was carried out in 60 g of $CF_3OCFClCF_2Cl$ as a solvent.

Trichloroethylene conversion was 87% while selectivity to $CHClF\!\!-\!\!CCl_2F$ was 50%.

Other products obtained in the process and their relative quantities were: $F(C_2Cl_3H)_2F$ (21%) and $CF_2ClCFCl_2$ (16%).

Comparative Example 2

The same reaction described in Example 1 was carried out in 68 g of $CFCl_3$ as a solvent.

Trichloroethylene conversion was 92% while selectivity to $CHClF\!\!-\!\!CCl_2F$ was 57%.

Other products obtained in the process and their relative quantities were: $F(C_2Cl_3H)_2F$ (15%) and $CF_2ClCFCl_2$ (18%).

Example 2

In a 250 ml stainless steel reactor containing 37 g of anhydrous hydrogen fluoride (aHF) kept under vigorous stirring at −45° C., 1,2-dichloroethylene (6 ml/h) and fluorine (1.75 Nl/h diluted with 4.5 Nl/h oh helium) were fed for 4 hours; after this period, the crude mixture was transferred in a stainless steel cylinder and the organic layer was analyzed.

The conversion of 1,2-dichloroethylene was 87% while the selectivity towards the formation of $CHClF\!\!-\!\!CHClF$ was 83%.

Other products obtained in the process and their relative quantities were: $F(C_2Cl_2H_2)_2F$ (5%), $CClF_2CHClF$ (5%), $CHCl_2CHClF$ (5%).

Comparative Example 2

The same reaction described in Example 2 was carried out in 54 g of $CF_3OCFClCF_2Cl$ as a solvent.

1,2-dichloroethylene conversion was 82% while selectivity to CHClF—CHClF was 49%.

Other products obtained in the process and their relative quantities were: F(C$_2$Cl$_2$H$_2$)$_2$F (29%), CClF$_2$CHClF (11%), CHCl$_2$CHClF (4%).

Possible modifications and/or additions may be made by those skilled in the art to the hereinabove disclosed and illustrated embodiments while remaining within the scope of the following claims.

The invention claimed is:

1. A process for the fluorination of haloolefins, the process comprising: continuously and simultaneously feeding into a reaction vessel: a first feed comprising an amount of elemental fluorine and a second feed comprising an amount of a haloolefin of formula (I):

$$CXR^1=CYR^2 \qquad (I),$$

wherein: $R^1$ is selected from the group consisting of F, Cl, Br, I, $R_{f1}$, and $OR_{f1}$; $R^2$ is selected from the group consisting of H, F, Cl, Br, I, $R_{f2}$, and $OR_{f2}$; X is selected from the group consisting of H, F, Cl, Br, and I; Y is selected from the group consisting of H, F, Cl, Br, and I; and $R_{f1}$ and $R_{f2}$, equal to or different from each other, are independently selected from a straight-chain or branched $C_1$-$C_{20}$ fluoroalkyl or a $C_1$-$C_{20}$ fluorooxyalkyl comprising one or more than one catenary oxygen atoms, wherein the reaction vessel contains anhydrous HF.

2. The process according to claim 1 wherein said $R^1$ is selected from the group consisting of F, Cl, $R_{f1}$, and $OR_{f1}$; said $R^2$ is selected from the group consisting of H, F, Cl, $R_{f2}$, and $OR_{f2}$; said X is selected from the group consisting of H, F, and Cl; and said Y is selected from the group consisting of H, F, and Cl.

3. The process according to claim 1 wherein said $R_{f1}$ and said $R_{f2}$ are perfluorinated.

4. The process according to claim 1 wherein said Y is H.

5. The process according to claim 4 wherein when said X is H then said $R^2$ is selected from F or Cl.

6. The process according to claim 1 wherein the olefin is selected from the group consisting of CH$_2$=CCl$_2$, CHCl=CCl$_2$, CHCl=CHCl, CFCl=CHF, CF$_3$OCH=CFCl, CF$_3$OCCl=CHF, and CF$_3$CCl=CF$_2$.

7. The process according to claim 1, wherein said process is carried out at a temperature in the range of from −90 to 0° C.

8. The process according to claim 1, wherein said $R_{f1}$ and said $R_{f2}$, together with the carbons to which they are attached, comprise a fluorinated cycloalkyl structure.

9. The process according to claim 1, wherein the first feed comprises elemental fluorine gas in a concentration of from 20% to 60% by volume.

10. The process according to claim 1, wherein the amount of elemental fluorine is equal to a stoichiometric amount necessary to convert all carbon-carbon double bonds in the amount of haloolefin to carbon-carbon single bonds.

* * * * *